(12) United States Patent
Johnson

(10) Patent No.: US 8,021,700 B1
(45) Date of Patent: Sep. 20, 2011

(54) TOPICAL SKIN SALVE AND ASSOCIATED USE THEREFOR

(76) Inventor: Wayne Johnson, Blanding, UT (US)

( * ) Notice: Subject to any disclaimer, the term of this patent is extended or adjusted under 35 U.S.C. 154(b) by 0 days.

(21) Appl. No.: 12/455,072

(22) Filed: May 28, 2009

(51) Int. Cl.
| | |
|---|---|
| A61K 36/00 | (2006.01) |
| A61K 31/00 | (2006.01) |
| A61K 35/00 | (2006.01) |
| A61K 31/355 | (2006.01) |
| A61K 31/11 | (2006.01) |

(52) U.S. Cl. .................. 424/725; 424/195.18; 514/458; 514/969

(58) Field of Classification Search .................. None
See application file for complete search history.

(56) References Cited

U.S. PATENT DOCUMENTS

| | | | |
|---|---|---|---|
| 4,454,118 A | 6/1984 | Johnson | |
| 4,946,832 A | 8/1990 | Goode et al. | |
| 5,045,058 A | 9/1991 | Demetrakopoulos | |
| 5,244,679 A * | 9/1993 | Freston | 424/659 |
| 5,997,889 A | 12/1999 | Durr et al. | |
| 6,419,936 B1 * | 7/2002 | Schmoyer | 424/401 |
| 6,809,079 B2 | 10/2004 | Southard et al. | |
| 2006/0122282 A1 | 6/2006 | Leonard | |

FOREIGN PATENT DOCUMENTS

| | | | |
|---|---|---|---|
| CA | 1263605 A | * | 12/1989 |
| WO | WO 02/051358 A | * | 7/2002 |

OTHER PUBLICATIONS

Tablespoon, Wikipedia, accessed on Sep. 4, 2010, pp. 1-3.*
How many ounces does one egg yolk have, Answer.com, accessed on Sep. 4, 2010, pp. 1-4.*
Hygroscopic, Rationale for use of biotene mouth care products rather than Vaseline, accessed on Sep. 4, 2010, pp. 1.*

* cited by examiner

*Primary Examiner* — Qiuwen Mi
(74) *Attorney, Agent, or Firm* — Robert C. Montgomery

(57) ABSTRACT

A general healing ointment for use on cracked lips, rashes, burns and the like is herein disclosed. The ointment is manufactured from an all natural blend of petroleum jelly, vitamin E cream and oil, cocoa butter, and pine pitch. It provides relief for a variety of ailments such as cracked skin, cold sores, rashes, acne, boils, and the like. It is readily absorbed by the skin and not visible to others, but won't dry out the skin afterwards.

4 Claims, No Drawings

TOPICAL SKIN SALVE AND ASSOCIATED USE THEREFOR

RELATED APPLICATIONS

The present invention was first described in a notarized Official Record of Invention on May 19, 2008, that is on file at the offices of Montgomery Patent and Design, LLC, the entire disclosures of which are incorporated herein by reference.

FIELD OF THE INVENTION

The present invention relates generally to topical skin applications and, more particularly, to a topical skin salve composition for moisturizing and soothing the skin.

BACKGROUND OF THE INVENTION

On any given day, just about everyone suffers from some sort of skin ailment ranging from dry skin, acne, rashes, poison ivy, athlete's foot and the like. Such ailments are not surprising when considering that the skin is not only the largest organ on the human body but is also the one (1) exposed to the harsh environment. As such, manufacturers have responded with a wide range of creams, ointments, balms, and the like, with each one targeted at a specific ailment. This approach yields not only a medicine cabinet full of bottles, tubes, jars, sprays and the like, but also leads to confusion as to which one is the best to treat their current skin ailment. Also, such solutions are full of chemicals which may cause an allergic reaction to the user as well. Many of these chemical additives can discolor the skin, can stain clothing, or even lead to other allergic reactions. Additionally, many of these products don't provide long term relief to skin ailments and require regular application in order to be effective.

Among the attempts to address these problems are several U.S. patents, including U.S. Pat. Nos.: 4,454,118; 4,946,832; 5,045,058; 5,997,889; 6,809,079; and U.S. published application number 2006/0122282.

While these devices fulfill their respective, particular objectives, each of these references suffers from one or more of the aforementioned disadvantages. Accordingly, there exists a need for a means by which various skin and lip ailments can be treated using a natural and simple compound. The development of present invention substantially departs from the conventional solutions and in doing so fulfills this need.

SUMMARY OF THE INVENTION

In view of the foregoing references, the inventor recognized the aforementioned inherent problems and observed that there is a need for a means provide an all natural topical skin composition that is simple, easy to apply, and highly effective and thus, the object of the present invention is to solve the aforementioned disadvantages.

To achieve the above objectives, it is an object of the present invention to provide a topical skin salve composition for moisturizing and soothing a user's skin comprising a hygroscopic mixture comprising an emollient substance, a paraffin substance, an antioxidant substance, and an aromatic compound including pine tar pitch that is adapted to be applied directly to the user skin.

Another object of the composition is to provide an emollient substance comprising cocoa butter for extending a storage life of the hygroscopic mixture.

Yet still another object of the composition is to provide a paraffin substance comprising petroleum jelly.

Yet still another object of the composition is to provide an antioxidant substance comprising vitamin E cream and vitamin E oil.

Yet still another object of the composition is to provide a hydroscopic mixture comprising thirty-two fluid ounces of the aromatic compound, one ounce of the emollient substance, four ounces of the antioxidant substance, and five ounces of the paraffin substance.

Yet still another object of the composition is to provide a method for preparing a topical skin salve composition for moisturizing and soothing a user skin comprising the steps of: obtaining preparation materials and placing the pine pitch in a cooking vessel and heating to a temperature between three hundred fifty and four hundred degrees Fahrenheit (300-400° F.) then straining the pine pitch through a double layer of cheesecloth. Next the strained solution of the pine pitch is added to the cocoa butter and the vitamin E cream and vitamin E oil. The petroleum jelly is added to the strained pine pitch solution and mixed well until a hydroscopic mixture is obtained which is cooled prior to use.

Yet still another object of the composition is to provide a method of utilizing the composition comprising applying the hydroscopic mixture to the skin as desired that provides a simple, but effective way of healing a wide variety of skin and lip ailments in an almost miraculous manner which is quick, easy and effective.

Further objects and advantages of the composition will become apparent from a consideration of the drawings and ensuing description.

DETAILED DESCRIPTION OF THE ESSENTIAL COMPOSITION

The essential composition herein refers to a topical skin salve composition, thereby providing an unctuous remedial substance for application to an exterior portion of a person's body.

The term "emollient" herein refers to any composition or a property thereof any composition that is hygroscopic and prevents dryness and otherwise moisturizes the application area.

The term "all-natural" herein refers to components of the present composition that have been extracted or otherwise derived from naturally occurring sources that are unrefined or unprocessed.

The essential composition is made of all natural ingredients, promotes healing of the skin, and retains moisture within the skin. The essential composition also leaves the skin feeling soft. The essential composition of the present invention comprises a skin salve for topical application to a user. Preferably, the topical composition is to be applied to areas of the skin that have been damaged by the elements or that are rough.

Typically, the preferred essential composition of the present invention involves the formulaic mixture of an emollient, paraffin, and an antioxidant.

More specifically, the preferred essential composition of the present invention comprises a formulaic blend pine pitch as an aromatic compound, cocoa butter as an emollient, petroleum jelly as a paraffin, and vitamin E (tocopherol) in the form of a cream and oil as an antioxidant.

The inclusion of cocoa butter in the essential composition allows for extended storage life of the essential composition.

The ingredients of the composition are prepared in the manner described below and applied to the surface of the skin where desired.

An example of a preferred essential composition of the present invention is prepared a follows:

| Component | Amount |
| --- | --- |
| Pine (*Pinus*) Tar Pitch | 32 fluid oz. |
| Theobroma Oil (Cocoa Butter) | 1 oz. |
| Vitamin E cream (tocopherol) | 4 oz. |
| Vitamin E oil (tocopherol) | 4 oz. |
| Petroleum Jelly (soft paraffin) | 5 oz. |

It is envisioned that other styles and configurations of the present invention can be easily incorporated into the teachings of the present invention, and only one (1) particular configuration shall be shown and described for purposes of clarity and disclosure and not by way of limitation of scope.

OPERATION AND USAGE OF THE PREFERRED EMBODIMENT

The preferred embodiment of the present invention can be utilized by the common user in a simple and effortless manner with little or no training. The preparation and processing of individual ingredients may be achieved by performing the following steps:

1. Pine Pitch Preparation—placing pine pitch in a cooking vessel and heating to a temperature between three hundred fifty and four hundred degrees Fahrenheit (350-400° F.); straining pine pitch through a double layer of cheesecloth; and, retaining the strained solution.

2. Final Preparation—adding cocoa butter, vitamin E cream, vitamin E oil, and petroleum jelly thereto the strained pine pitch solution and mixing well; allowing the mixture to cool; and, using the essential compound immediately or storing it in a jar or can.

The essential composition is envisioned to be purchased in locations where consumer care products are typically sold. After initial purchase of the essential composition, preparation is envisioned to take place as follows: identifying an area of the skin that is to be treated with the essential composition; confirming that the essential composition is cool enough to not burn the skin; applying a small amount of the essential composition to the desired skin area; rubbing the essential composition into the desired skin area; enjoying the sensation and benefits of the essential composition; and, reapplying as necessary.

The foregoing descriptions of specific embodiments of the present invention have been presented for purposes of illustration and description. They are not intended to be exhaustive or to limit the invention and method of use to the precise forms disclosed. Obviously many modifications and variations are possible in light of the above teaching. The embodiment was chosen and described in order to best explain the principles of the invention and its practical application, and to thereby enable others skilled in the art to best utilize the invention and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present invention.

What is claimed is:

1. A topical skin salve composition for moisturizing and soothing a user skin, said topical skin salve composition comprising: a hygroscopic mixture comprising:
    thirty-two (32) fluid ounces of an aromatic compound including pine tar pitch;
    one (1) ounce of an emollient substance;
    four (4) ounces of an antioxidant substance; and
    five (5) ounces of a paraffin substance, wherein said hygroscopic mixture is applied directly to the user skin.

2. The topical skin salve composition of claim 1, wherein said emollient substance comprises cocoa butter for extending a storage life of said hygroscopic mixture.

3. The topical skin salve composition of claim 1, wherein said paraffin substance comprises petroleum jelly.

4. The topical skin salve composition of claim 1, wherein said antioxidant substance comprises vitamin E cream and vitamin E oil.

* * * * *